United States Patent [19]

Kim et al.

[11] 4,179,402

[45] Dec. 18, 1979

[54] RESIN-METAL-LIGAND COMPOSITION

[75] Inventors: Leo Kim; Timm E. Paxson; Sunny C. Tang, all of Houston, Tex.

[73] Assignee: Shell Oil Company, Houston, Tex.

[21] Appl. No.: 905,813

[22] Filed: May 15, 1978

[51] Int. Cl.$^2$ .................. B01J 31/08; B01J 31/10
[52] U.S. Cl. .................. 252/431 C; 585/277; 585/520; 585/645; 585/734; 252/429 R; 252/431 R; 252/431 N; 252/431 P; 260/449.6 R; 260/449 R; 560/233; 260/604 HF
[58] Field of Search ........... 252/429 R, 431 R, 431 C, 252/431 N, 431 P

[56] References Cited

U.S. PATENT DOCUMENTS

| | | | |
|---|---|---|---|
| 3,726,809 | 4/1973 | Allum et al. | 252/431 P |
| 3,847,997 | 11/1974 | Allen | 252/431 P X |
| 3,872,026 | 3/1975 | Dunn | 252/431 N X |
| 3,900,557 | 8/1975 | Strathdee | 252/431 P X |
| 3,907,852 | 9/1975 | Oswald et al. | 252/431 N X |
| 3,980,583 | 9/1976 | Mitchell et al. | 252/431 N X |
| 3,998,864 | 12/1976 | Trevillyan | 252/431 P X |
| 4,045,493 | 8/1977 | Trevillyan | 252/431 P X |
| 4,053,534 | 10/1977 | Mitchell et al. | 260/683.15 R |
| 4,072,720 | 2/1978 | Haag et al. | 252/431 N X |
| 4,098,727 | 7/1978 | Haag et al. | 252/431 R X |
| 4,111,856 | 9/1978 | Haag et al. | 252/431 N X |

OTHER PUBLICATIONS

Pittman et al., "Polymer-Bound Catalysts," Chemtech, Sep. 1973, pp. 560-566.
Lapporte et al., J. Org. Chem., 28 (Jul. 1963), pp. 1947-1948.

*Primary Examiner*—Patrick Garvin
*Attorney, Agent, or Firm*—Howard W. Haworth

[57] ABSTRACT

A composition comprising an ion exchange resin, a metal selected from the transition group of elements bound to said resin and an organic linking compound which has at least one moiety which is ionically bonded to said resin and which further has at least one moiety which is coordinately bonded to said metal.

9 Claims, No Drawings

RESIN-METAL-LIGAND COMPOSITION

BACKGROUND OF THE INVENTION

1. Field of the Invention

This invention relates to a composition comprising an ion exchange resin with a ligand ionically bonded thereto with the ligand coordinately bonded to a transition element and with the transition element also bonded to the resin.

2. The Prior Art

The use of heterogeneous catalysts over homogeneous catalysts has several advantages such as allowing the use of fixed beds, ease of separation of catalyst from the product and catalyst recovery and regeneration.

Traditionally, to produce heterogeneous catalysts from metals of the transition element series, these metals have been deposited on inert supports such as alumina or slica. More recently metal catalysts have been covalently attached to inert resin backbones by use of diphenylphosphine or other ligands which are attached directly to the polymer and coordinately bonded to the metal. Typical examples of this type are found in U.S. Pat. No. 3,998,864, issued Dec. 21, 1976, and in Pittman et al, Chemtech, p. 560–566, 1973.

Application Ser. No. 861,916, filed Dec. 19, 1977, disclosed a composition comprising an ion exchange resin with an organic linking compound ionically bonded thereto and with the linking compound further coordinately bonded to a transition element metal. The composition of this invention, on the other hand, not only has the transition element bonded to the linking compound but also to the resin. This dual bonding of the metal provides additional stability. The composition of this invention is much more leach resistant with regard to the transition metal than conventional heterogeneous transition metal catalysts. The materials of this invention are also relatively simple to prepare using commercially available compounds. Their preparations involve no exotic conditions and often times may be carried out in an aqueous solvent system and the resins may be easily stripped of metal and ligands for isolation of the metal species and regeneration of the catalyst. The resin based catalysts of this invention have unique selectivity-reactivity properties when compared to their homogeneous analogues.

SUMMARY OF THE INVENTION

The invention provides a method whereby a metal is attached to an ion exchange resin with each metal atom being bonded to the resin two different ways, directly bonded and bonded via an intermediate linking ligand. Specifically, this invention is directed to the composition which comprises (a) an ion exchange regin, (b) a metal selected from the transition group of elements and which is directly bonded, either coordinately or ionically, to the ion exchange resin and in addition (c) a linking compound which has at least one moiety coordinately bonded to the metal and further has at least one moiety which is ionically bonded to the ion exchange resin. The compositions of this invention are particularly useful as heterogeneous catalysts and are particularly resistant to the leaching out of the metal catalyst component.

DESCRIPTION OF THE PREFERRED EMBODIMENTS

The ion exchange resins utilized in the composition of this invention are well known in the art and are readily available commercially. These are in the gel form or are macroporous and are either strongly acidic, weakly acidic, strongly basic, intermediate basic, weakly basic, or mixed acid-base. The strong acid resins typically have base resins of cross-linked styrene, styrene-divinylbenzene, phenol-formaldehyde, benzene-formaldehyde, having functional sulfonic or phosphonic acid groups attached thereto. Also suitable are the fluorinated alkyl sulfonic resins containing the —$CFSO_3H$ groups as, for example, the NAFION ® type resins supplied by E.I. DuPont DeNemours. The weak acid resins are those with carboxylic acid groups and are typically acrylic acid derivatives such as, for example, those resins prepared by the copolymerization of methacrylic acid and divinylbenzene. Another weak acid resin is th chelating type which is a styrene-divinylbenzene copolymer containing iminodiacetic acid functional groups which can serve as an anion exchanger at very low pH. The basic resins typically have base resins of cross-linked styrene, styrene-divinylbenzene, phenol-formaldehyde, benzene-formaldehyde, epoxypolyamine, phenolic-polyamine having functional amine, either primary, secondary, tertiary or quaternary, or pyridinium groups attached thereto. Typical examples of suitable commercially supplied resins are given in Table I (reference: Bio-Rad Laboratories Catalogue, Chromatography, Electrophoresis, Immunochemistry and Membrane Filtration, Price List C, Mar. 1977, p. 11).

TABLE I

| Type and Exchange Group | Bio-Rad Analytical Grade Ion Exchange Resins | Dow Chem. Company "Dowex" | Diamond Shamrock "Duolite" | Rohm & Haas Co. "Amberlite" | Permutit Company (England) | Permutit Company (U.S.A.) |
|---|---|---|---|---|---|---|
| Anion exchange resins | | | | | | |
| Strongly Basic, polystyrene $\phi$-$CH_2N^+(CH_3)_3Cl^-$ | AG 1-X1 | 1-X1$^a$ | | | DeAcidite FF (lightly crosslinked) | S-100 |
| | AG 1-X2 | 1-X2$^a$ | | | | |
| | AG 1-X4 | 1-X4$^{ab}$ | A-101D | IRA-401 | | |
| | AG 1-X8 | 1-X8$^{ab}$ | | IRA-400 CG-400 | DeAcidite FF | |
| | AG 1-X10 | 1-X10$^a$ | | IRA-425 | | |
| | AG 21K | 21K$^a$ | | IRA-402 | | |
| $\phi$-$CH_2N^+(CH_3)_2(C_2H_4OH)$ $Cl^-$ | AG 2-X4 | 2-X4$^a$ | A-102D | | | S-200 |
| | AG 2-X8 | 2-X8$^a$ | | IRA-410 | | A-580 |
| [pyridinium structure with $CH_3Cl^-$ and $CH_3$] | AG 2-X10 Bio-Rex 9 | | | | | |
| Intermediate Base, epoxypolyamine | | | | | | |

TABLE I-continued

| Type and Exchange Group | Bio-Rad Analytical Grade Ion Exchange Resins | Dow Chem. Company "Dowex" | Diamond Shamrock "Duolite" | Rohm & Haas Co. "Amberlite" | Permutit Company (England) | Permutit Company (U.S.A.) |
|---|---|---|---|---|---|---|
| R—N+(CH₃)₂Cl⁻ and R—N+(CH₃)₂(C₂H₄OH) Cl⁻ | Bio-Rex 5 | | A-30B | | F | S-310 S-380 |
| Weakly Basic, polystyrene or phenolic polyamine φ-CH₂N+(R)₂Cl⁻ | AG 3-X4 A | WGR$^a$ | A-6 A-7$^b$ A-4F | IR-45 IR-4B IRA-68 | G | S-300 S-350 |
| Cation exchange resins | | | | | | |
| Strong Acidic, phenolic R—CH₂SO₃⁻ H+ | Bio-Rex 40 | | C-3$^{ab}$ | | Zoecarb 215 | |
| Strong Acidic, polystyrene φ-SO₃⁻ H+ | AG 50W-X1 AG 50W-X2 AG 50W-X4 | 50W-X1$^a$ 50W-X2$^a$ 50W-X4$^a$ | | IR-116 IR-118 | Zeocarb 225 (X4) | |
| | AG 50W-X8 | 50W-X8$^{ab}$ | C-20 | IR-120 CG-120 | Zeocarb 225 | Permutit Q |
| | AG 50W-X10 AG 50W-X12 AG 50W-X16 | 50W-X10$^a$ 50W-X12$^{ab}$ 50W-X16$^a$ | C-20X10 C-20X12 | IR-122 IR-124 | | Q-100 Q-110 Q-130 |
| Weakly Acidic, acrylic R—COO⁻Na+ | Bio-Rex 70 | | CC-3 | IRC-50 CG-50 | Zeocarb 226 | Q-210 |
| Weakly Acidic, chelating resin, polystyrene φ-CH₂N⟨CH₂COO⁻H+ / CH₂COO⁻H+ | Chelex 100 | A-1$^a$ | | | | |
| Macroporous resins | | | | | | |
| Strong Base, polystyrene φ-CH₂N+(CH₃)₃ Cl⁻ | AG MP-1 | MSA-1 | A-161 | IRA-900 | | |
| Strong Acid, polystyrene φ-SO₃⁻ H+ | AG MP-50 | MSC-1 | C-250 | 200 | | |
| Mixed bed resins | | | | | | |
| φ-SO₃⁻H+ & φ-CH₂N+(CH₃)₃OH⁻ | AG 501-X8 | | GMP-331 G | MB-1 | Bio-Demineralit | M-100 |

The preferred resin choice for the composition of this invention will depend on the particular ionically bondable moiety utilized on the linking compound as well as on the particular use envisioned for the compositon. For example, if the composition were used in liquid-phase catalsis, the composition and pH of the liquid would determine the preferred resin to be utilized.

The linking compound is hydrocarbyl, i.e., alkyl, aryl, or mixtures of aryl and alkyl components, which can be either cyclic or acyclic or mixtures thereof containing from 1 to about 100 carbon atoms, preferably from about 3 to about 80 carbon atoms and has at least two moieties containing an atom other than carbon.

At least one moiety is in the ionic or ionizable form and is compatible with the exchange group on the ion exchange resin, i.e., when the exchange group is acidic the resin-compatible ionic moiety on the linking compound is basic-derived and vice versa. The acidic-derived resin compatible ion moiety is derived from carboxylic acid ($RCO_2^-$), phosphonic acid ($RPO(OH)O^-$), phosphinic acid ($R_2POO^-$), sulfenic acid ($RSO^-$), sulfinic acid ($RSOO^-$), sulfonic acid ($RSO_2O^-$), boronic acid ($RSOO^-$), sulfonic acid ($RSO_2O^-$), boronic acid ($RB(OH)O^-$), boronous acid ($RBO^-$), The basic-derived resin compatible ion moiety is monohydrocarbyl ammonium ($RN^+H_3$), dihydrocarbyl ammonium ($R_2N^+H_2$), trihydrocarbyl ammonium ($R_3N^+H$), quaternary ammonium ($R_4N^+$), pyridinium ($RC_5H_4N^+R_1$), phosphonium ($R_4P^+$), arsonium ($R_4As^+$), and sulfonium ($R_3S^+$).

The linking compound may have more than one of the ionic moieties. It may be polyfunctional, for example, in carboxylate ion, in phosphonate ion, in sulfonate ion, in quaternary ammonium ion, in pyridinium and the like. The polyfunctional group may be the same or different.

At least one other moiety of the linking compound has an atom capable of complexing with metals from the transition element series, and consists of trivalent nitrogen, trivalent phosphorus, trivalent arsenic, trivalent bismuth, and trivalent antimony.

The three valences of the complexing atoms may be satisfied by any organic radical; saturated or unsaturated aliphatic, and/or saturated or unsaturated heterocyclic and/or aromatic radicals. These radicals may contain any functional group such as carbonyl, nitro, and hydroxy groups as well as saturated and unsaturated alkyl groups and the radical may be bonded to the complexing atom directly through a carbon-complexing atom linkage or through an electronegative atom such as oxygen or sulfur.

It is also suitable for a simple organic radical to satisfy more than one of the valences of the complexing atom, thereby forming a heterocyclic compound with the trivalent complexing atom. For example, an alkylene radical may satisfy two of the valences thereby forming a cyclic compound. Another example would be the alkylene dioxy radical to form a cyclic compound where oxygen atoms link an alkylene radical to the complexing atom. In these two examples, the third valence may be satisfied by any other organic radical.

The linking compound may have more than one of the metal-complexing moieties. It may be, for example, polydentate in phosphorus atom, e.g., it may be bi- or tridentate, having two or three phosphorus atoms. It may have mixed complexing atoms, e.g., a phosphorus and arsenic atom or two phosphorus atoms and one nitrogen atom, etc.

The trivalent nitrogen atom will be present as an amine, i.e., as a primary, secondary, tertiary, quaternary amine or as pyridine or cyanide. The trivalent phosphorus will be present as phosphine ($R_3P$), phosphinite ($ROPR_2$), phosphonite ($(RO)_2PR$ and phosphite ($(RO)_3P$. Correspondingly, trivalent arsenic will be available as arsine, arsinite, arsonite and arsenite; trivalent bismuth as bismuthine, bismuthinite, bismuthonite and bismuthite; and trivalent antimony as stibine, stibinite, stibonite and stibite. The preferred complexing atoms are phosphorus and nitrogen. The tertiary amines, phosphines, arsines and stibines and bismuthines have a marked tendency to form nonionic complexes with metals.

When the linking compound is polydentate in an ionizable heteroatom, it is understood that there will be a statistical distribution of the ionized atoms upon quaternization or protonation. For example, if one mole of a linking compound which contains 3 amine groups is protonated with 2 moles of HCl, then some of the molecules of the linking compound will have 3 quaternized amine groups, some will have 2 and some will have 1, but on the average there will be 2 quaternized amino groups per molecule. It is further understood from general principles of orgaic chemistry that unit charges resulting from quaternization and protonation can be distributed as partial charges over several heteroatoms in a linking compound molecule.

Thus the linking compound as reacted in the composition of this invention will have at least one protonized or quaternized heteroatom and at least one heteroatom complexed with a transition element metal. Suitable linking compounds utilized in making the composition of the invention include but are not limited to the following examples:

tris(dimethylamino)phosphine
tris(diethylamino)phosphine
tris(diisopropylamino)phosphine
tris(methylethylamino)phosphine
tris(p-dimethylaminophenyl)phosphine
tris(p-diethylaminophenyl)phosphine
tris(p-methylethylaminophenyl)phosphine
tris(o-dimethylaminophenyl)phosphine
tris(m-dimethylaminophenyl)phosphine
tris(dimethylaminoethyl)phosphine
tris(dimethylaminoethyl)phosphite
ethylbis(diphenylphosphinoethyl)amine Substitution of phosphinites, phosphonites, phosphites for the phosphine in the above compounds as well as arsines, arsinites, arsonites, arsenites, bismuthenes, bismuthinites, bismuthonites, bismuthites, stibines, stibinites, stibonites, stibites and amines produces linking compounds useful in preparing the compositions of this invention. Other suitable compounds are:

2-(P,P-diphenylphosphino)benzoic acid
tris(beta-aminoethyl)amine
2-chloronicotinic acid, and 2-carboxypyridine
1,1-dimethyl-4-phenylpiperazinium salt
2,2'-alkylarsino-1,1'-diphenylamine
2-(P,P-dicyclohexylphosphino)benzoic acid
beta-(dicyclohexylphosphino)propionic acid
1,4-(P,P-diphenylphosphino)benzene
2-diphenylphosphino-3-carboxy-2-butene
2-(P,P-diphenylphosphino)benzene sulfonic acid
2-amino-s-triazine
1-diphenylphosphino-2-diphenylphosphinoethane
tris-(N,N-diarylaminoethyl)phosphite
tris(N,N-diarylamino)phosphine
3-(dialkylphosphino)benzene phosphonic acid The metals which are bonded to the ion exchange resin and also complexed with the linking compound are selected from the transition elements of the Periodic Table and preferably are selected from Groups IVB, VB, VIB, VIIB, VIII, IB and IIB, technetium excluded, i.e., preferred metals are:

TABLE II

| IVB | VB | VIB | VIIB | VIII | | | IB | IIB |
|-----|----|----|------|------|----|----|----|-----|
| Ti | V | Cr | Mn | Fe | Co | Ni | Cu | Zn |
| Zr | Nb | Mo | — | Ru | Rh | Pd | Ag | Cd |
| Hf | Ta | W | Re | Os | Ir | Pt | Au | Hg |

Preferred metals are from Groups VIB, VIIB, VIII and IB.

The complexed metals can be in various oxidation states. See "Complexes of the Transition Metals with Phosphines, Arsines and Stibines", by G. Booth, Adv. Inorg. Nucl. Chem., 6, 1–69 (1964) for a comprehensive description of complexes. For example, the Booth reference cites the following oxidation states for metals complexed with phosphines.

TABLE III

| Metal | Oxidation State for Stable Phosphine Complexes |
|-------|-----------------------------------------------|
| Ti | 4 |
| Zr | 4 |
| Hf | 4 |
| V | 0, 3, 4 |
| Cr | 0, 2, 3 |
| Mo | 0, 1, 2, 3, 4 |
| W | 0, 1, 2, 3, 4 |
| Mn | 0, 1 |
| Re | 0, 1, 2, 3, 4, 5 |
| Fe | 0, 1, 2, 3 |
| Ru | 0, 2, 3, 4 |
| Os | 2, 3, 4 |
| Co | 1, 2, 3 |
| Rh | 0, 1, 3 |
| Ir | 1, 3 |
| Ni | 0, 1, 2, 3 |
| Pd | −0, 2 |
| Pt | 0, 2 |
| Cu | 1, 3 |
| Ag | 1 |
| Au | 1, 3. |

Articles dealing with the complexing of amines with metals are "Inorganic Complexes", Jorgensen, C. K., Academic Press 1963, chap. 4 and "Chemistry Coordination Compounds", Bailer (Ed.), Am. Chem. Soc. Monograph Series 131, 1956. The above references cite the following oxidation states for metals complexed with amines.

TABLE IV

| Metal | Oxidation State of Stable Amine Complexes |
|-------|-------------------------------------------|
| Cr | 0, 1, 2, 3 |
| Mo | 0, 3 |
| W | 2 and 3 (polynuclear), 4 (mononuclear) |

TABLE IV-continued

| Metal | Oxidation State of Stable Amine Complexes |
|---|---|
| Mn | 2 |
| Re | 3, 5 |
| Fe | 2, 3 |
| Ru | 2, 3 |
| Os | 2, 3, 4 |
| Co | 2, 3 |
| Rh | 3 |
| Ir | 3, 4 |
| Ni | 0, 2 |
| Pd | 2 |
| Pt | 0, 2, 4 |
| Cu | 2 |
| Ag | 1, 2 |
| Au | 3 |

The metal is not only complexed with the linking compound but is also bonded directly to the ion exchange resin. The metal will be typically ionically bonded to the resin when the resin has acid functional groups attached thereto, such as for examples, sulfuric acid groups, phosphoric acid groups, fluorinated alkyl sulfonic acid groups, carboxylic acid groups, and iminodiacetic acid groups. Covalent bonding occurs when the ion exchange resin has basic functional groups attached thereto such as, for example, amino groups, either primary, secondary, tertiary or quarternary, or pyridinium groups or iminodiacetic acid groups.

The composition of the invention may have more than one transition element metal present. The composition may also have the metal(s) co-complexed with other ligands in addition to the linking compound. For example, from the above-noted Booth reference the metal complexed moiety of the composition could have the following form and still be within the scope of the invention, i.e., $M_y$ $M_z'$ $O_A$ $H_B$ $X_C$ $(CN^-)_D(CO)_E(NO)_F(Cp)_G(Py)_H(Acac)_I(AsR_3)_J(NR_3)_K(PR_3)_L(SNX_3^-)_M(GeX_3^-)_M(Carb)_NP_Q$-(Funct.)$_R$ $M_y$ = metal in oxidation state shown in Table II or Table III y = 0 to n mononuclear to polynuclear cluster $M_z'$ = metal in oxidation state shown in Table II or Table III z = 0 to n mononuclear or mixed metal polynuclear cluster where n is an integer greater than 0 when y>0 and z>0

O = oxygen where A = 0 to n
H = hydrogen where B = 0 to n
X = halide F, Cl, Br, I; where C = 0 to 5
$(CN^-)$ = cyanide where D = 0 to 5 when y+z=1 or D = 1 to n when y+z>1
(CO) = carbonyl where E = 0 to 5 when y+z=1 or E = 1 to n when y+z>1
(NO) = nitrosyl where F = 0 to 5 when y+z=1 or F = 1 to n when y+z>1
Cp = cyclopentadienyl where G = 0 to 3 when w=z=1 or G = 1 to n when y+z>1
Py = pyridine where H = 0 to 5 when y+z=1 or H = 1 to n when y+z>1
Acac = acetylacetonate where I = 0 to 3 when y+z=1 or I = 1 to n when y+z>1
$(AsR_3)$ = arsines, where R = H, alkyl or aryl and J = 0 to 5 when y+z=1 or J = 1 to n when y+z>1 the arsine also may be of the chelating type or contain mixed donating atoms e.g.

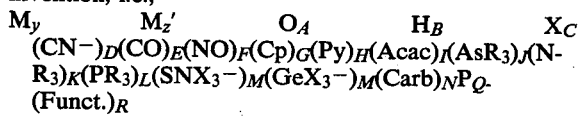

$(NR_3)$ = amines, where R = H, alkyl, or aryl and K = 0 to 5 when y+z=1 or K = 1 to n when y+z>1 as with arsines, a chelating or mixed donor chelating ligand may be employed.

$(PR_3)$ = phosphines were R = H, alkyl, or aryl, and L = 0 to 5 when y+z=1 or L = 1 to n when y+z>1 as with arsines, and amines, a chelating ligand may be employed.

$(SnX_3^-)$ or $(GeX_3^-)$ = trihalostannyl or trihalogermyl where X = F, Cl, Br, I and M = 0 to 5 when y+z=1 or M = 1 to n when y+z>1

(Carb) = carboxylate where N = 0 to 5 when y+z=1 or N = 1 to n when y+z>1

P = the bridging moiety/ligand between the metal and the resin support and Q = 1 to n.

(Funct.) = function ion exchange group attached to the ion-exchange resin and R = 1 to n The compositions of the invention find use as catalysts in many chemical processes. Illustrative examples are the use of compositions containing rhodium or ruthenium complexes in hydroformylation-carbonylation, hydrogenation, isomerization and Fischer-Tropsch reactions. Compositions containing cobalt complexes are useful in hydroformylation, carbonylation, hydrogenation and isomerization reactions. Compositions containing molybdenum complexes are used in disproportionation (metathesis) and isomerization reactions. Compositions containing palladium and platinum complexes are useful in hydroformylation, carbonylation, isomerization, hydrogenation and oligomerization/dimerization reactions. Compositions containing nickel complexes are useful in hydrogenation, oligomerization/dimerization reactions. Compositions containing tungsten or rhenium complexes are useful in metathesis reactions. Other reactions that can utilize the compositions of the invention will be apparent to one skilled in the art.

The composition of this invention and preparation thereof is described by the following illustrative embodiments which are provided for illustration and are not construed as limiting the invention.

ILLUSTRATIVE EMBODIMENTS

The catalyst preparation procedures described were carried out in nitrogen-filled dry boxes. The solvent benzene was purified by distillation over $CaH_2$, all other solvents were of reagent-grade and used as supplied. The phosphine $[(CH_3)_2NC_6H_4]_3P$, was used as supplied. The quaternized aminophosphines were prepared by reaction of one equivalent of $CH_3Br$ with an aminophosphine in toluene solution at room temperature. The quaternized aminophosphine precipitated readily from the toluene solution. The resins are indicated by (resin backbone)-(exchange group), e.g. a sulfonated styrene-divinylbenzene resin would be (styrene-divinylbenzene)-($SO_3^-$), etc. Ph, $C_6H_5$ and $\phi$-are used as abbreviations for phenyl; —$\phi$— and $C_6H_4$ indicated p-substituted benzene moieties.

PREPARATION OF THE COMPOSITIONS OF THIS INVENTION

EXAMPLE 1

Preparation of carboxylated acrylic resin/Rh III.

A 10 gram quantity of carboxylated acrylic resin Bio-Rex 70 (10.2 meq/gm) was stirred with 1 liter of 1N NaCl at room temperature for 60 minutes. The solid was collected by filtration and the procedure repeated. The material was then washed thoroughly with deionized water and 23.4 ml of a 0.5%w solution of $Rh(NO_3)_3$ in water. The combined materials were stirred overnight at room temperature. At the end of this time period, the material was collected by vacuum filtration and washed with deionized water until the washings were colorless. The material was air dried.

EXAMPLE 2

Preparation of carboxylated acrylic resin/Rh III/methyl quaternized $[(CH_3)_2NC_6H_4]_3P$ compound.

A 9.0 gram lot of the material prepared in Example 1 was added to a solution of 2 liters of acetone-water (1:1 v/v) which contained 2.0 gm (4.1 mmol) of methyl quaternized $[(CH_3)_2NC_6H_4]_3P$. These materials were stirred overnight at room temperature and the solids collected by vacuum filtration. The material was then washed with an acetone solution, a water solution, and finally air dried. The material was analyzed to contain 0.10%w Rh.

EXAMPLE 3

Preparation of phosphinated styrene-divinylbenzene resin/Rh III.

A 10 gram lot of Bio Rex 63 (microreticular gel. phosphinated, 6.6 meq/gm) was treated as described in Example 1.

EXAMPLE 4

Preparation of phosphinated styrene-divinylbenzene resin/Rh III/methyl quaternized $[(CH_3)_2NC_6H_4]_3P$ compound.

A 9.0 gram lot of the material prepared in Example 3 was treated with the quaternized aminophosphine as described in Example 3. Rh analysis 0.45%w.

EXAMPLE 5

Preparation of sulfonated styrene-divinylbenzene resin/Rh III.

A 10 gram lot of Rohm and Haas XN1010Na (macroreticular resin, 3.6 meq/gm) was treated in a manner similar to that described in Example 1.

EXAMPLE 6

Preparation of sulfonated styrene-divinylbenzene resin/Rh III/quaternized $[(CH_3)_2NC_6H_4]_3P$ compound.

A 10.0 gm lot of the material prepared in Example 5 was treated with the quaternized aminophosphine as described in Example 2. Rh analysis 0.45%w.

EXAMPLE 7

Preparation of sulfonated styrene-divinylbenzene resin/$[(CH_3)_2NC_6H_4]_3P$/platinum-tin cationic complex composition.

The aminophosphine $[(CH_3)_2NC_6H_4]_3P$ (14.0 g, 35.8 mmol) was dissolved in 1000 ml warm benzene, cooled to room temperature, and filtered into a 2-l round-bottomed flask quickly. 10.0 G of XN1010OH$^+$ ion-exchange resin was added, and the mixture stirred magnetically on side of flask for 72 hours. The resin was then filtered, washed with benzene and vacuum dried in oven (40° C.). Analysis showed a resin/ligand material having the approximate formula (styrene-divinylbenzene)-$(SO_3^-)_{1.5}[([(CH_3)_2NC_6H_4]_3P)(H^+)_{1.5}]$.

A $CH_2Cl_2$ solution of the platinum complex PtCl(CO) $[P(C_6H_5)_3]_2^+ClO_4^-$ was prepared by the addition of 0.3 g (1.4 mmol) of anhydrous $AgClO_4$ to a solution of $PtCl_2[P(C_6H_5)_3]_2$(1.05 g, 1.3 mmol) dissolved in 40 ml of CO-saturated $CH_2Cl_2$. The $CH_2Cl_2$ solution was stirred under 40 psi of CO for ½ hr, and filtered. To the resultant filtrate was added 5.0 g of the XN1010OH$^+$ resin/ligand material prepared as described above, mixed together on a rotator for approximately 70 hours and filtered. The resultant resin material was added to a solution of 5.0 g (22.2 mmol) of $SnCl_2.2H_2O$ dissolved in 450 ml of acetone, mixed on rotator for 1 hour, filtered, Soxhlet-extracted with refluxing benzene for 4 hours, and dried in vacuum oven overnight at approximatey 40° C. Analysis showed a composition having the approximate formula (styrene-divinylbenzene)-$(SO_3^-)_{1.5}[[(CH_3)_2NC_6H_4]_3-P(H^+)_{1.5}][(PtCl(CO)[P(C_6H_5)_3]_2)(SnCl_2)^+]_{0.07}$. The analytical results are shown in Table V below.

TABLE V

ANALYTICAL ANALYSIS OF PLATINUM-TIN/ PHOSPHINE/RESIN CATALYST

|    | Neutron Activation w % | Elemental wt % | Analysis Relative Molar Value (carbon = 100) |
|----|----|----|----|
| C  | —   | 57.8 | 100 |
| H  | —   | 5.56 | 116 |
| S  | —   | 7.05 | 4.6 |
| N  | —   | 1.32 | 2.0 |
| P  | 1.6 | 1.59 | 1.1 |
| Sn | 7.0 | 5.82 | 1.0 |
| Cl | —   | 3.55 | 2.1 |
| Pt | 2.0 | 1.83 | 0.20 |

EXAMPLE 8

Preparation of sulfonated styrene-divinylbenzene resin/methyl-quaternized $([(CH_3)_2NC_6H_4]_3P$/platinum-tin cationic complex compositon. The quaternized aminophosphine $([(CH_3)_2NC_6H_4]_3P)(CH_3^+)Br^-$(10.4 g (21.1 mmol)) was dissolved in 1900 ml of an acetone/$H_2O$ (12:7 v/v) solution. 12.0 Grams of XN1010Na ion-exchange resin (prepared by exhaustive ion-exchange of XN1010H$^+$ with 10 l of 1N NaCl or when the pH of the effluent wash was neutral) was added. The mixture was side-stirred for 48 hours, filtered with suction, and the resin washed with 5×100 deionized $H_2O$, then vacuum dried in an oven overnight (45° C.). Analysis showed a resin/ligand material having the approximate formula (styrene-divinylbenzene)-$(SO_3^-)[([(CH_3)_2NC_6H_4]_3P)(CH_3^+)]$.

The material of this example was prepared in a similar manner as in Example 7 except that the XN1010Na resin/ligand material prepared as described above was used. Analysis showed a composition having the approximate formula (styrene-divinylbenzene)-(SO$_3^-$)[([(CH$_3$)$_2$NC$_6$H$_4$]$_3$P)(-CH$_3^+$)][(PtCl(CO)[P(C$_6$H$_5$)$_3$]$_2$)(SnCl$_2$)$^+$]$_{0.02}$.

PROCESS UTILIZING THE COMPOSITIONS OF THIS INVENTION

EXAMPLE 9

Hydroformylation of Hexene

To a 300-ml, ss Magnedrive autoclave (stirred at 600 rpm) was added 70 ml of benzene, 2.0 ml of n-decane (internal standard), 20.0 ml (160 mmol) of 1-hexene, and 1.0 g of the catalyst as listed below. The solution was deoxygenated with nitrogen. Synthesis gas ((CO/H$_2$, 1:1) was then charged to the reactor and the reactor was heated to the appropriate temperature listed below. Conversions and selectivities were obtained by gas chromatography; leach rates by atomic absorption. The leach rates are extremely low, in many cases undetectable. Results are given in Table VI.

TABLE VI
HYDROFORMYLATION WITH PLATINUM/TIN CATALYSTS

| Catalyst | Temp. °C. | Pressure psig | Time hr | Conv. % |
|---|---|---|---|---|
| Example 7 | 80 | 3000 | 10 | 16.4 |
|  |  |  | 24 | 39.1 |
|  |  |  | 44 | 52.7 |
| Example 7 | 100 | 1500 | 10 | 19.3 |
|  |  |  | 24 | 35.6 |
|  |  |  | 44 | 40.0 |
| Example 7 | 100 | 3000 | 4 | 15.1 |
|  |  |  | 10.5 | 36.1 |
| Example 8 | 100 | 3000 | 20 | 21.6 |
| a | 80 | 3000 | 10 | 3.4 |
|  |  |  | 24 | 4.7 |
|  |  |  | 45 | 2.4 |

| Selectivities, % | | | |
|---|---|---|---|
| | c$_7$-ald | Pt leach | Rate |

TABLE VI-continued
HYDROFORMYLATION WITH PLATINUM/TIN CATALYSTS

| c$_7$-ald | hexane | linearity(%) | ppm/hr | m/m/hr |
|---|---|---|---|---|
| 96.5 | 3.5 | 94.3 | | |
| 96.3 | 3.7 | 93.9 | | |
| 95.5 | 4.5 | 93.2 | undetectable | 170 |
| 96.3 | 3.7 | 94.0 | | |
| 94.5 | 5.2 | 93.1 | | |
| 93.5 | 6.2 | 92.4 | undetectable | 170 |
| 95.2 | 2.4 | 91.1 | | |
| 97.2 | 2.1 | 88.8 | 0.03 | 180 |
| 97.6 | 0.9 | 77.8 | undetectable | |
| 95.5 | 4.5 | 90.4 | | |
| 94.6 | 5.4 | 88.2 | — | 19 |
| 93.7 | 6.3 | 81.6 | | |

$^a$Homogeneous reaction, amount of catalyst (PtCl$_2$(P$\phi_3$)$_2$, SnCl$_2$) identical to that on Example 7 above.

EXAMPLE 10

Hydroformylation of 1,5-Cyclooctadiene

To a 300-ml, ss-Magnedrive autoclave (stirred at 600 rpm) was added 15 gm (138 mmol) of 1,5-cyclooctadiene, 70 mls of THF solvent, 2 gm (10.1 mmol) of n-tetradecone (marker), and 0.5 gm of catalyst material. The solution was deoxygenated with nitrogen. Synthesis gas (CO/H$_2$; 1:1 1000–1500 psig) was then charged to the reactor and the reactor was heated to 80°–90° C. Conversions and selectivities were obtained by gas chromatrography; leach rates by atomic absorption spectroscopy. Results are given in Table VII.

TABLE VII
HYDROFORMYLATION OF 1,5-CYCLOOCTADIENE

| Catalyst | Time (hr) | Total Press. (psig) Ave. | Conv. (%) | 1,3-COD |
|---|---|---|---|---|
| Example 6 | 1.0 | 1300 | 17.0 | 50.8 |
|  | 2.0 |  | 34.2 | 48.7 |
|  | 3.0 |  | 80.6 | 45.5 |
|  | 4.0 |  | 96.3 | 43.2 |
|  | 5.0 |  | 99.1 | 45.6 |
| Exampl;e 6 (first recycle) | 5.0 |  | 11.8 | 61.1 |
|  | 6.0 |  | 25.7 | 65.3 |
| Example 2 | 4.0 | 1050 | 28.4 | 90.3 |
| Example 4 | 4.0 | 1000 | 18.6 | 85.2 |

| Selectivities (%) | | | Total to | Mat. Bal. | Amt. Rh. Catalyst | Leaching |
|---|---|---|---|---|---|---|
| 4-CHOC$_8$ | x-CHOC$_8$= | CHOC$_8$° | CHOC$_8$= | (%) | (mmol) | (ppm/hr) |
| 49.2 | 0 | 0 | 49.2 |  | 0.0214 |  |
| 51.3 | 0 | 0 | 51.3 |  |  |  |
| 53.5 | 1.0 | trace | 54.5 |  |  |  |
| 52.7 | 3.7 | 0.3 | 56.4 |  |  |  |
| 48.2 | 6.2 | 0.3 | 54.4 | 106 |  | 2.5 |
| 38.9 | 0 | 0 | 38.9 |  |  |  |
| 34.7 | 0 | 0 | 34.7 | 86 | 0.0118 | 0.17 |
| 9.7 | 0 | 0 | 9.7 | 91 | 0.534 | 0.2 |
| 14.5 | 0.4 | 0 | 14.9 | 92 | 0.0219 | 1.0 |

We claim as our invention:
1. A composition comprising:
 (a) an ion exchange resin having a strongly acidic, weakly acidic, or mixed acid-base type functional group;
 (b) an element, selected from the transition group of elements and which is directly bonded either coordinately or ionically to the ion exchange resin; and

(c) an organic linking compound of from 1 to about 100 carbon atoms which has at least one moiety selected from the group consisting of trivalent nitrogen, trivalent phosphorus, trivalent arsenic, trivalent bismuth and trivalent antimony which is coordinately bonded to said element and further has at least one moiety selected from the group consisting of monohydrocarboyl ammonium, dihydrocarbyl ammonium, trihydrocarbyl ammonium, quaternary ammonium, pyridinium, phosphinium, arsenium and sulfonium ion which is ionically bonded to the ion exchange resin.

2. A composition comprising:
(a) an ion exchange resin having a basic-type functional group,
(b) an element selected from the transition group of elements and which is directly bonded either coordinately or ionically to the ion exchange resin; and
(c) an organic linking compound of from 1 to about 100 carbon atoms which has at least one moiety containing a heteroatom selected from the group consisting of trivalent nitrogen, trivalent phosphorus, trivalent arsenic, trivalent bismuth and trivalent antimony which is coordinately bonded to said element and further has at least one moiety derived from the group consisting of carboxylic acid, phosphonic acid, phosphinic acid, sulfenic acid, sulfinic acid, sulfonic acid, boronic acid and boronous acid which is ionically bonded to the ion exchange resin.

3. The composition of claim 1 wherein the functional group of the ion exchange resin is selected from the group consisting of sulfonic acid, fluorinated alkyl sulfonic acid, phosphonic acid, carboxylic acid and aminocarboxylic acid, the ionically bonded moiety is selected from the group consisting of monohydrocarbyl ammonium, dihydrocarbyl ammonium, trihydrocarbyl ammonium, quaternary ammonium, pydridinium and phosphonium, the coordinately bonded moiety contains a heteroatom selected from the group consisting of trivalent nitrogen and trivalent phosphorus and the metal is selected from Group VIB, VIIB, VIII, and IB.

4. The composition of claim 3 wherein the ion exchange resin has a backbone selected from the group consisting of polymerized styrene, styrene-divinylbenzene, phenol-formaldehyde, benzene-formaldehyde, acrylic acid and methacrylic acid.

5. The composition of claim 2 wherein the functional group of the ion exchange resin is selected from the group consisting of primary, secondary, tertiary, quaternary amine and pyridinium, the ionically bonded moiety is selected from the group consisting of trivalent nitrogen and trivalent phosphorus and the metal is selected from Group VIB, VIIB, VIII and IB.

6. The composition of claim 5 wherein the ion exchange resin has a backbone selected from the group consisting of polymerized styrene, styrene-divinylbenzene, phenol-formaldehyde, benzene-formaldehyde, epoxypolyamine and phenolic-polyamine.

7. The composition of claim 1 wherein the element is selected from the group consisting of cobalt, ruthenium, molybdenum, tungsten, tin, platinum, palladium and rhodium.

8. The composition of claim 3 wherein the element is selected from the group consisting of cobalt, ruthenium, molybdenum, tungsten, tin, platinum, palladium and rhodium.

9. The composition of claim 2 wherein the element is selected from the group consisting of cobalt, ruthenium, molybdenum, tungsten, tin, platinum, palladium and rhodium.

* * * * *

UNITED STATES PATENT AND TRADEMARK OFFICE
CERTIFICATE OF CORRECTION

PATENT NO. : 4,179,402
DATED : December 18, 1979
INVENTOR(S) : LEO KIM, TIMM E. PAXSON, SUNNY C. TANG It is certified that error appears in the above-identified patent and that said Letters Patent are hereby corrected as shown below:

In column 13, line 10, delete "phosphinium" and substitute therefor -- phosphonium --.

In column 13, line 11, delete "arsenium" and substitute therefor -- arsonium --.

Signed and Sealed this

Third Day of February 1981

[SEAL]

Attest:

Attesting Officer

RENE D. TEGTMEYER

Acting Commissioner of Patents and Trademarks